(12) United States Patent
Xi et al.

(10) Patent No.: US 9,167,887 B2
(45) Date of Patent: Oct. 27, 2015

(54) ORAL CARE IMPLEMENT

(75) Inventors: Wen Jin Xi, Shanghai (CN); Yu Liu, Wuxi (CN); Jian Rong Zhou, Yangzhou (CN)

(73) Assignee: COLGATE-PALMOLIVE COMPANY, New York, NY (US)

( * ) Notice: Subject to any disclaimer, the term of this patent is extended or adjusted under 35 U.S.C. 154(b) by 74 days.

(21) Appl. No.: 13/997,023

(22) PCT Filed: Dec. 21, 2010

(86) PCT No.: PCT/CN2010/002111
§ 371 (c)(1),
(2), (4) Date: Jun. 21, 2013

(87) PCT Pub. No.: WO2012/083491
PCT Pub. Date: Jun. 28, 2012

(65) Prior Publication Data
US 2013/0276252 A1    Oct. 24, 2013

(51) Int. Cl.
*A46B 7/06* (2006.01)
*A46B 9/04* (2006.01)
(Continued)

(52) U.S. Cl.
CPC ............ *A46B 9/04* (2013.01); *A46B 5/0029* (2013.01); *A46B 7/06* (2013.01); *A46B 9/06* (2013.01); *A46B 15/0075* (2013.01); *A46D 3/00* (2013.01); *A46B 15/0081* (2013.01);
(Continued)

(58) Field of Classification Search
CPC ........ A61B 17/244; A61H 13/00; A46B 7/02; A46B 7/06; A46B 9/04; A46B 9/06; A46B 15/0075; A46B 15/0081; A46B 2200/1026; A46B 2200/1066

USPC ......... 15/110, 111, 167.1, 188, 201; 601/139, 601/141; 606/161
See application file for complete search history.

(56) References Cited

U.S. PATENT DOCUMENTS 1,840,246 A    1/1932 Newman
1,860,924 A    5/1932 Cooke
(Continued)

FOREIGN PATENT DOCUMENTS

EP    0 976 345    2/2000
JP    2002199938    7/2002
(Continued)

OTHER PUBLICATIONS

International Search Report and the Written Opinion of the International Searching Authority issued in International Application PCT/CN2010/002111 mailed Oct. 13, 2011.

*Primary Examiner* — Mark Spisich

(57) ABSTRACT

An oral care implement, such as a toothbrush (100), comprises a handle (110) and a head (120). A plurality of tooth cleaning elements (130) may be provided on a front surface (121) of the head (120). The head (120) is formed by a plurality of spaced-apart segments (140-145) made of a rigid material. The segments (140-145) are isolated from one another by channels (157-159B) containing an elastomeric material (146) that flexibly connects the segments (140-145) together. The oral care implement further comprises an elastomeric soft tissue cleaner (200) located on a rear surface (122) of the head (120) opposite the front surface (121) of the head (120). Each of the segments (140-145) comprises a protuberance (163-169) made of the rigid material that extends through the elastomeric soft tissue cleaner (200) and is exposed therethrough.

21 Claims, 15 Drawing Sheets

(51) Int. Cl.
*A46B 9/06* (2006.01)
*A46B 15/00* (2006.01)
*A46B 5/00* (2006.01)
*A46D 3/00* (2006.01)
*A61B 17/24* (2006.01)

(52) U.S. Cl.
CPC  *A46B 2200/1026* (2013.01); *A46B 2200/1066* (2013.01); *A61B 17/244* (2013.01)

(56) References Cited

U.S. PATENT DOCUMENTS

| | | | |
|---|---|---|---|
| 2,438,268 A | 3/1948 | Bressler | |
| 2,650,383 A | 9/1953 | Bressler | |
| 2,676,350 A | 4/1954 | Bressler | |
| 3,188,672 A | 6/1965 | Gary | |
| 3,253,292 A | 5/1966 | Herschensohn | |
| 4,566,145 A | 1/1986 | Wachtel | |
| 5,651,158 A | 7/1997 | Halm | |
| 5,758,383 A | 6/1998 | Hohlbein | |
| 5,802,656 A | 9/1998 | Dawson et al. | |
| 5,946,759 A * | 9/1999 | Cann | 15/167.1 |
| 5,970,564 A | 10/1999 | Inns et al. | |
| 5,991,959 A | 11/1999 | Raven et al. | |
| 6,115,870 A * | 9/2000 | Solanki et al. | 15/167.1 |
| 6,219,874 B1 * | 4/2001 | van Gelder et al. | 15/167.1 |
| 6,327,735 B1 * | 12/2001 | Kramer | 15/167.1 |
| 7,024,720 B2 | 4/2006 | Moskovich et al. | |
| 7,143,462 B2 | 12/2006 | Hohlbein | |
| 7,322,067 B2 | 1/2008 | Hohlbein | |
| 7,594,293 B2 | 9/2009 | Xi et al. | |
| 7,707,676 B2 | 5/2010 | Solanki | |
| 7,707,677 B2 | 5/2010 | Moskovich et al. | |
| 7,721,376 B2 | 5/2010 | Hohlbein et al. | |
| 7,757,333 B2 * | 7/2010 | Battaglia | 15/167.1 |
| 7,908,699 B2 | 3/2011 | Hohlbein | |
| 8,523,888 B2 | 9/2013 | Gatzemeyer et al. | |
| 2001/0014991 A1 * | 8/2001 | Halm et al. | 15/167.1 |
| 2004/0134007 A1 * | 7/2004 | Davies | 15/110 |
| 2005/0210612 A1 | 9/2005 | Hohlbein et al. | |
| 2006/0026784 A1 | 2/2006 | Moskovich et al. | |
| 2006/0117508 A1 | 6/2006 | Hohlbein | |
| 2008/0052848 A1 | 3/2008 | Hohlbein | |
| 2008/0115305 A1 | 5/2008 | Battaglia | |
| 2008/0307596 A1 | 12/2008 | Hohlbein | |
| 2009/0188063 A1 | 7/2009 | Baertschi et al. | |
| 2010/0043162 A1 * | 2/2010 | Zimmermann et al. | 15/111 |
| 2010/0229316 A1 | 9/2010 | Hohlbein et al. | |

FOREIGN PATENT DOCUMENTS

| | | | |
|---|---|---|---|
| KR | 10-2005-0058524 | | 6/2005 |
| WO | 98/07349 | * | 2/1998 |
| WO | WO 98/27846 | | 7/1998 |

* cited by examiner

ORAL CARE IMPLEMENT

CROSS-REFERENCE TO RELATED PATENT APPLICATIONS

The present application is a U.S. national stage application under 35 U.S.C. §371 of PCT Application No. PCT/UN2010/002111, filed Dec. 21, 2010, the entirety of which is incorporated herein by reference.

FIELD OF THE INVENTION

The present invention relates generally to oral care implements, and specifically to oral care implements having a flexible head formed by a plurality of segments.

BACKGROUND OF THE INVENTION

A toothbrush is used to clean the teeth by removing plaque and debris from the tooth surfaces. Conventional toothbrushes having a flat bristle trim are limited in their ability to conform to the curvature of the teeth, to penetrate into the interproximal areas between the teeth, to sweep away the plaque and debris, and to clean along the gum line. Additionally, such toothbrushes have a limited ability to retain dentifrice for cleaning the teeth. During the brushing process, the dentifrice typically slips through the tufts of bristles and away from the contact between the bristles and the teeth. As a result, the dentifrice is often spread around the mouth, rather than being concentrated on the contact of the bristles with the teeth. Therefore, the efficiency of the cleaning process is reduced.

While substantial efforts have been made to modify the cleaning elements of toothbrushes to improve the efficiency of the oral cleaning process, the industry continues to pursue arrangements of cleaning elements that will improve upon the existing technology.

A number of attempts have been made to create flexible toothbrush heads that provide greater cleaning efficacy by allowing the head to flex, thereby allowing the bristles and other tooth cleaning elements to extend at various angles relative to one another. In one type of known flexible toothbrush head, the head is broken up into a plurality of segments that are flexible relative to one another and relative to the handle. However, the existing designs of many segmented toothbrush heads result in the head having either too much or not enough flexibility. Too much flexibility results in the head being unable to transmit sufficient pressure to the teeth or other oral surfaces via the bristles when the handle is subject to normal brushing forces. On the other hand, inadequate flexibility results in the segments (and thus the bristles) remaining substantially stationary, thereby defeating the purpose of having a flexible head.

More recently, the strategic arrangement and combination of tooth cleaning elements in the form of elastomeric cleaning elements and bristle tufts has become a more common way of improving cleaning efficiency. However, very little efforts have been made to coordinate the structure and arrangement of elastomeric cleaning elements on flexible toothbrush heads formed by a plurality of segments.

Elastomeric soft tissue cleaners, which are typically located on the rear surface of the toothbrush head, have also become quite popular. However, as with the tooth cleaning elements, very little effort has been expended to coordinate the structure of the soft tissue cleaner with the structure of flexible toothbrush heads utilizing a plurality of segments.

BRIEF SUMMARY OF THE INVENTION

The present invention is directed to an oral care implement, such as a toothbrush. In one aspect, the invention is directed to an oral care implement comprising a handle and a head. A plurality of tooth cleaning elements may be provided on a front surface of the head. The head is formed by a plurality of spaced-apart segments formed of a rigid material. The segments are isolated from one another by channels containing an elastomeric material that flexibly connects the segments together. The oral care implement further comprises an elastomeric soft tissue cleaner located on a rear surface of the head opposite the front surface of the head. Each of the segments comprises a protuberance that extends through the soft tissue cleanser and is exposed therethrough.

In one embodiment, the invention can be an oral care implement comprising: a handle; a head connected to the handle; a plurality of tooth cleaning elements extending from a front surface of the head; the head formed by a plurality of spaced-apart segments formed of a rigid material, the plurality of segments including a central segment and at least one peripheral segment arranged about the central segment, the at least one peripheral segment isolated from the central segment by a channel containing an elastomeric material, the elastomeric material flexibly connecting the at least one peripheral segment to the central segment; an elastomeric soft tissue cleaner located on a rear surface of the head opposite the front surface of the head; and the at least one peripheral segment and the central segment comprising at least one protuberance formed of the rigid material that extends through the elastomeric soft tissue cleanser so that a portion of the rigid material of the at least one protuberance is exposed.

In another embodiment, the invention can be an oral care implement comprising: a handle; a head connected to the handle; a plurality of tooth cleaning elements extending from a front surface of the head; the head formed by a plurality of spaced-apart segments formed of a rigid material, each of the segments isolated from one another by a channel containing an elastomeric material, the elastomeric material flexibly connecting the segments together; an elastomeric soft tissue cleaner located on a rear surface of the head opposite the front surface of the head; and each of the segments comprising at least one protuberance formed of the rigid material that extends through the elastomeric soft tissue cleanser so that a portion of the rigid material of the at least one protuberance is exposed.

In yet another embodiment, the invention can be an oral care implement comprising: a handle; a head connected to the handle; a plurality of tooth cleaning elements extending from a front surface of the head; the head formed by a skeleton formed of a rigid material, the skeleton comprising a plurality of spaced-apart segments and struts extending between the segments; an elastomeric material flexibly connecting the segments together; an elastomeric soft tissue cleaner located on a rear surface of the head opposite the front surface of the head; and each of the segments comprising at least one protuberance formed of the rigid material that extends through the elastomeric soft tissue cleanser so that a portion of the rigid material of the protuberance is exposed.

In still another embodiment, the invention can be a method of forming a head of an oral care implement comprising: a) forming a skeleton of a rigid material, the skeleton comprising a plurality of spaced-apart segments and struts extending between the segments, each of the segments comprising at least one protuberance formed of the rigid material that extends from a rear surface of the segment; b) positioning the skeleton in a cavity of a mold, the mold contacting a portion of each of the protuberances; and c) injecting an elastomeric material in liquid form into the cavity of the mold, the elastomeric material forming a soft tissue cleaner that covers the rear surfaces of the segments and the portions of the rigid material of the protuberances remain exposed through the soft tissue cleaner.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

This invention is capable of use in a broad array of oral care implements and hygiene products. The drawings illustrate one use of the invention and are not to be construed as the only embodiment of the invention. The present invention will become more fully understood from the detailed description and the accompanying drawings, wherein.

DETAILED DESCRIPTION OF THE INVENTION

The following description of the preferred embodiment(s) is merely exemplary in nature and is in no way intended to limit the invention, its application, or uses. In the following description, the invention is discussed in terms of a manual toothbrush incorporating the novel arrangement of cleaning elements. However, in other forms, the invention could be in the form of other oral care implements including a soft-tissue cleansing implement, a powered toothbrush, or other ansate implement designed for oral care.

Figure 1:
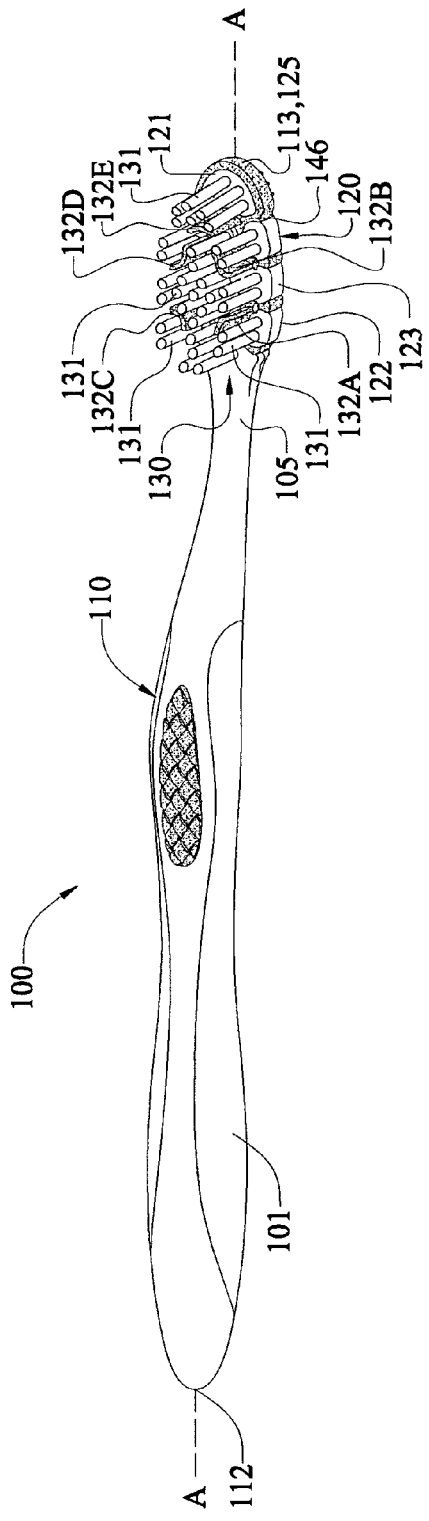
FIG. 1 is a front perspective view of an oral care implement, in the form of a toothbrush, according to one embodiment of the present invention.
Figure 2:
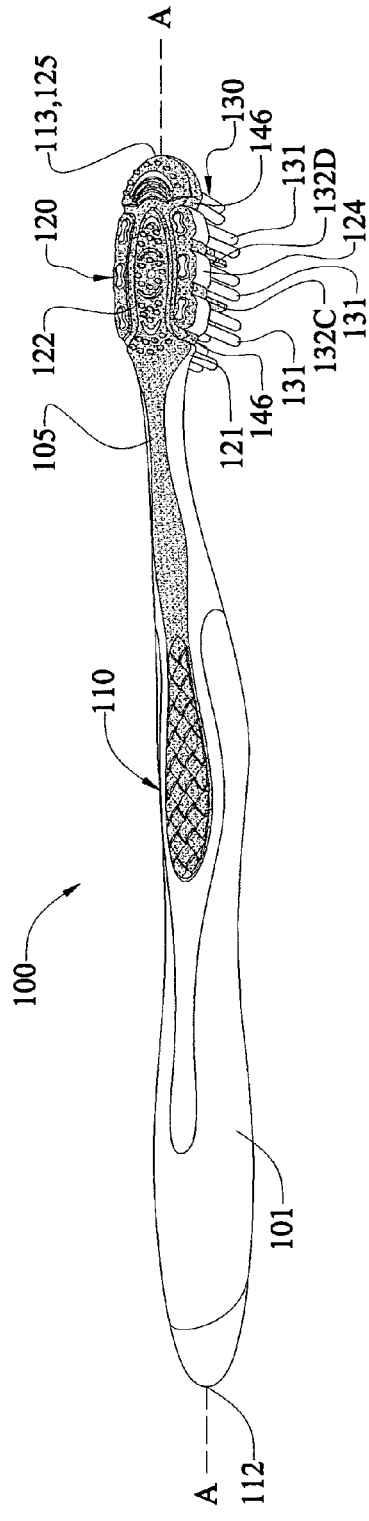
FIG. 2 is a rear perspective view of the toothbrush of FIG. 1.

Referring first to FIGS. 1-2, a toothbrush 100 is illustrated according to one embodiment of the present invention. The toothbrush 100 generally comprises a handle 110 and a head 120. The handle 110 provides the user with a mechanism by which he/she can readily grip and manipulate the toothbrush 100. The handle 110 may be formed of many different shapes, sizes, materials and by a variety of manufacturing methods that are well-known to those skilled in the art. If desired, the handle 110 may include a suitable textured grip 101 made of elastomeric material or can be a multi-part construction. Stated simply, unless specifically stated otherwise, the details of the handle 110 are not limiting of the present invention and, thus, require no further discussion for purposes of the present invention.

The toothbrush 100 extends from a proximal end 112 to a distal end 113 along a longitudinal axis A-A, a portion of which forms the longitudinal axis of the head 120. The head 120 is connected to a distal end 105 of the handle 110. As discussed in greater detail below, the skeleton of the head 120 is integrally formed with the handle 110 in certain embodiments of the invention thereby forming a single unitary structure. An injection molding, milling, machining or other suitable process can be used as is known in the art. However, in other embodiments, the handle 110 and the head 120 may be formed as separate components which are operably connected at a later stage of the manufacturing process by any suitable technique known in the art, including without limitation thermal welding, a tight-fit assembly, a coupling sleeve, adhesion, or fasteners. Whether the head 120 and handle 110 are of a unitary or multi-piece construction (including connection techniques) is not limiting of the present invention in all embodiments.

It should be noted at this time that relative terms such as distal, middle, proximal, upper, lower, top, bottom, left, right etc. are merely used to delineate relative positions of the components of the toothbrush 100 with respect to one another and are not intended to be in any further way limiting of the present invention.

The head 120 generally comprises a front surface 121 and a rear surface 122. The front surface 121 and the rear surface 122 of the head 120 can take on a wide variety of shapes and contours, none of which are limiting of the present invention. For example, the front and rear surfaces 121, 122 can be planar, contoured or combinations thereof. The head 120 also comprises a right lateral edge 123, a left lateral edge 124, and a distal edge 125, which collectively form the peripheral edge of the head 120 that connect the front and rear surfaces 121, 122. In the exemplified embodiment, the distal edge 125 is located at the distal end 113.

A plurality of cleaning elements 130 may extend from the front surface 121 of the head 120 for cleaning contact with an oral surface, preferably teeth. While the plurality of tooth cleaning elements 130 is particularly suited for brushing teeth, the plurality of tooth cleaning elements 130 can also be used to clean other surfaces of the oral cavity if desired. As used herein, the term "tooth cleaning element" is used in a generic sense to refer to any structure that can be used to clean or massage an oral surface through relative surface contact. Common examples of "tooth cleaning elements" include, without limitation, filament bristles, fiber bristles, nylon bristles, spiral bristles, rubber bristles, elastomeric protrusions, flexible polymer protrusions, co-extruded filaments, flag bristles, crimped bristles, anti-bacterial bristles and combinations thereof and/or structures containing such materials or combinations.

As discussed below, in the exemplified embodiment, the plurality of cleaning elements 130 comprises a plurality of bristle tufts 131 and a plurality of elastomeric cleaning elements 132A-E. In the exemplified embodiment, the elastomeric cleaning elements 132A-E are in the form of arcuate elastomeric walls. However, in certain other embodiments, the elastomeric cleaning elements 132A-E can be in the form of elastomeric fingers, linear elastomeric walls, and/or combinations thereof. The elastomeric cleaning elements 132A-E are formed of a suitable elastomeric material. In one embodiment, the elastomeric cleaning elements 132A-E are formed of a thermoplastic elastomer ("TPE"). Other suitable elastomeric materials include any biocompatible resilient material suitable for uses in an oral hygiene apparatus. To provide optimum comfort as well as cleaning benefits, the elastomeric material preferably has a hardness property in the range of A10 to A40 Shore hardness, and preferably A25 Shore hardness. One preferred elastomeric material is styrene-ethylene/butylene-styrene block copolymer (SEBS) manufactured by GLS Corporation. Nevertheless, SEBS material from other manufacturers or other materials within and outside the noted hardness range could be used.

Figure 3:
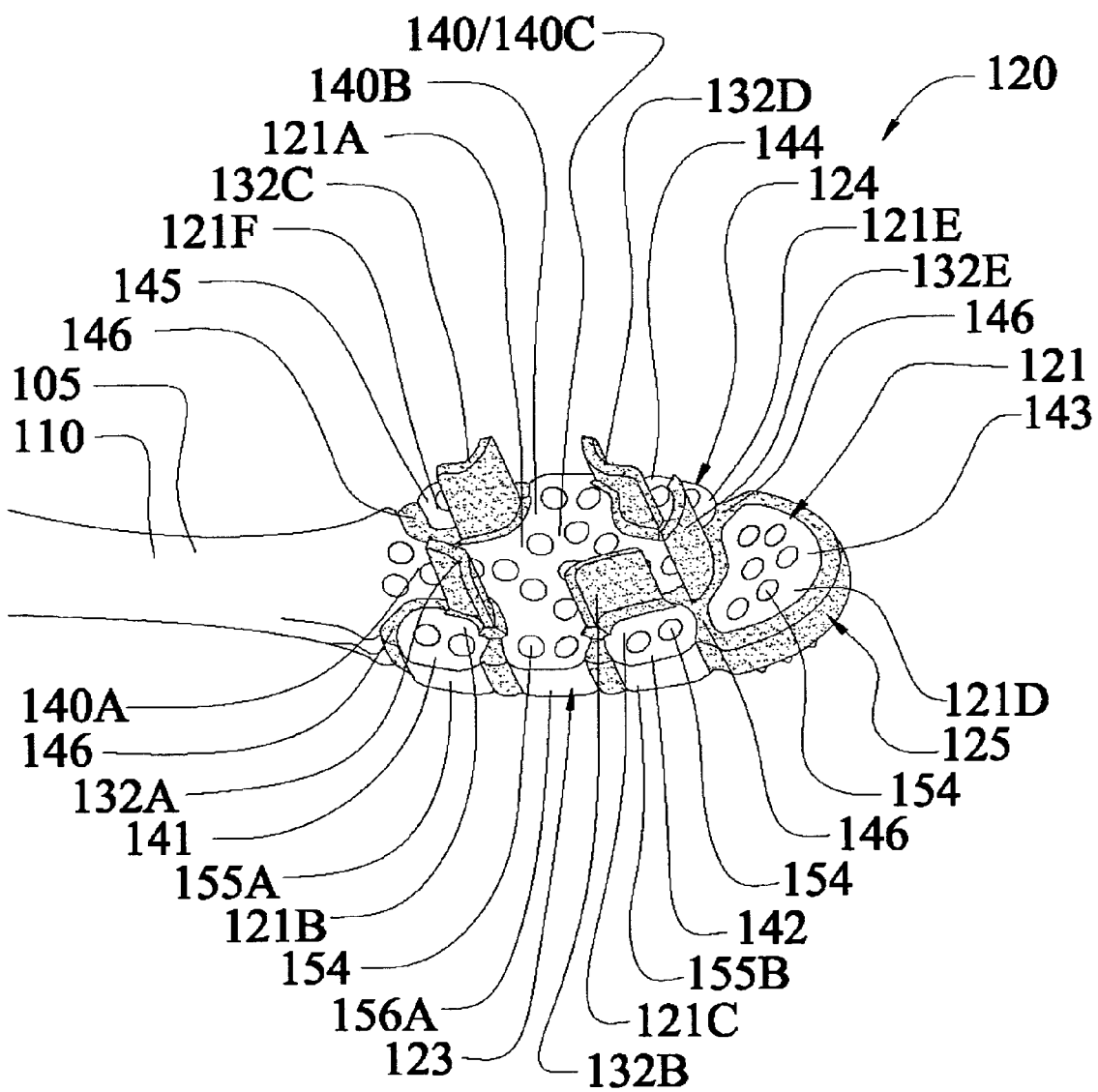
FIG. 3 is a front perspective view of the head of the toothbrush of FIG. 1 wherein the bristle tufts have been removed.
Figure 4:
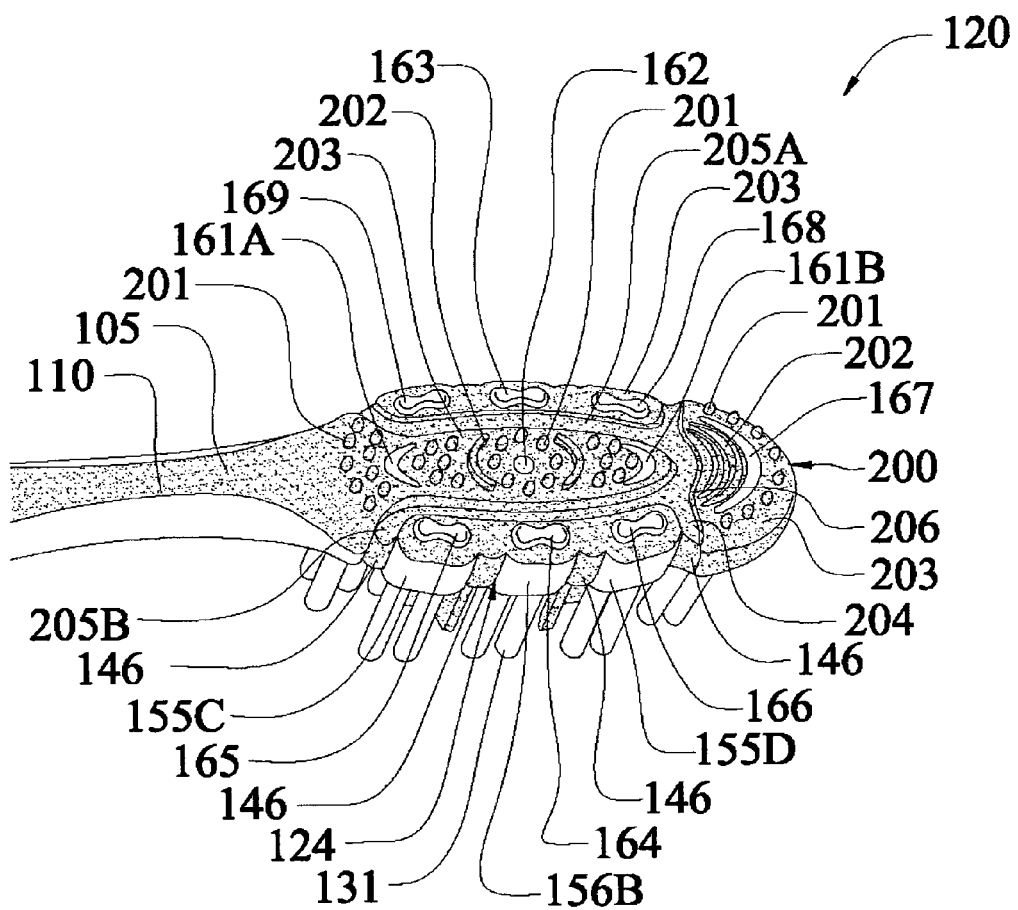
FIG. 4 is a rear perspective view of the head of the toothbrush of FIG. 1.
Figure 5:
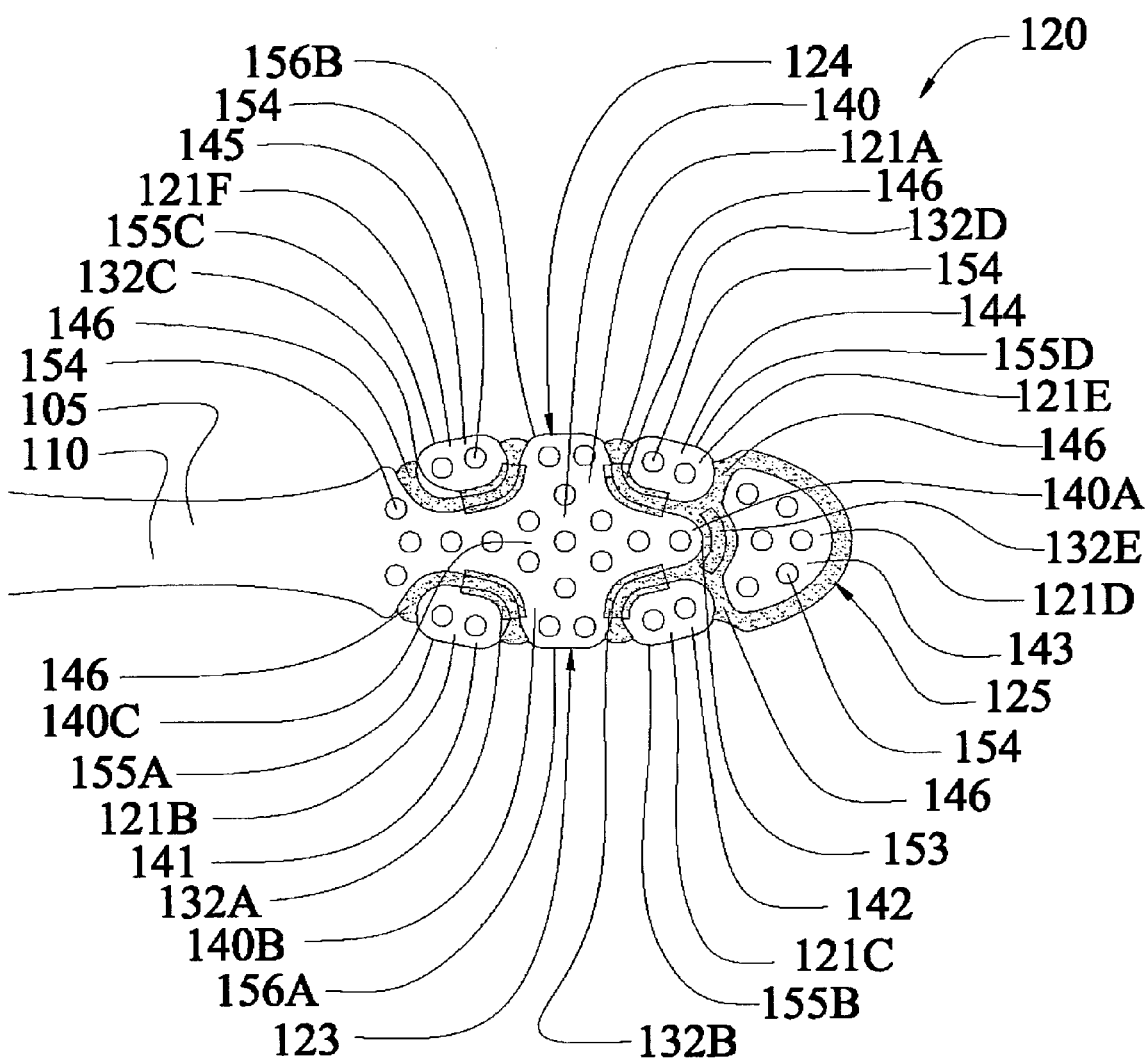
FIG. 5 is a front view of the head of the toothbrush of FIG. 1 wherein the bristle tufts have been removed.
Figure 6:
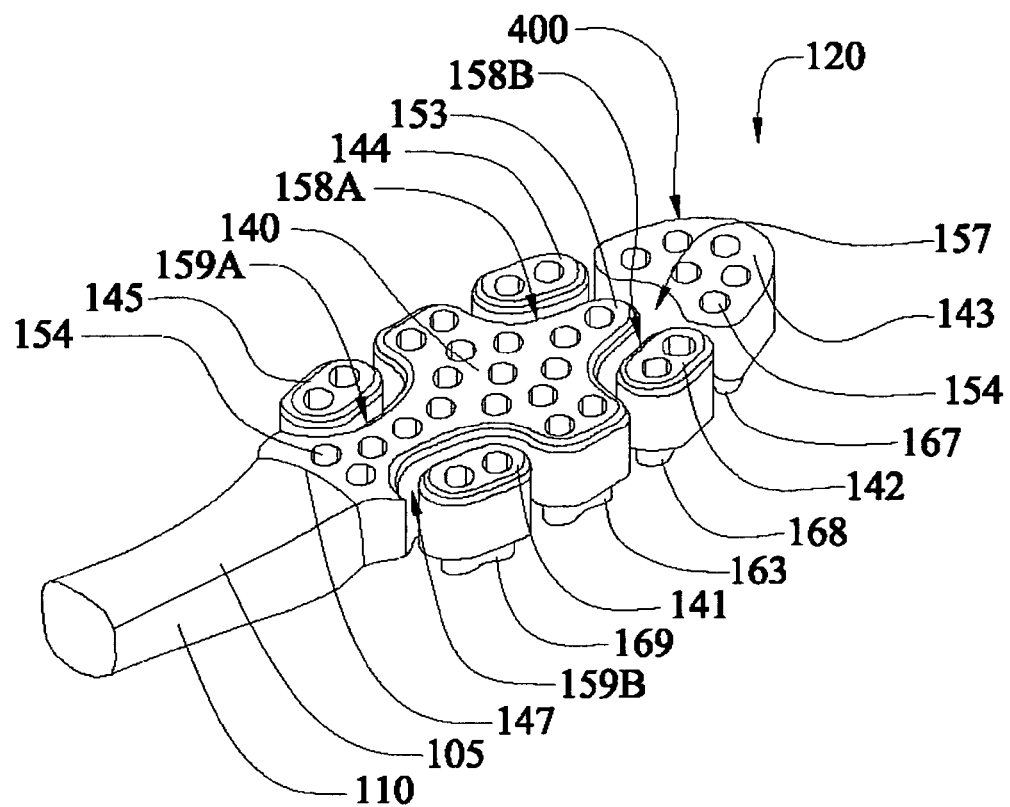
FIG. 6 is a front perspective view of the rigid material skeleton of the head of the toothbrush of FIG. 1.
Figure 7:
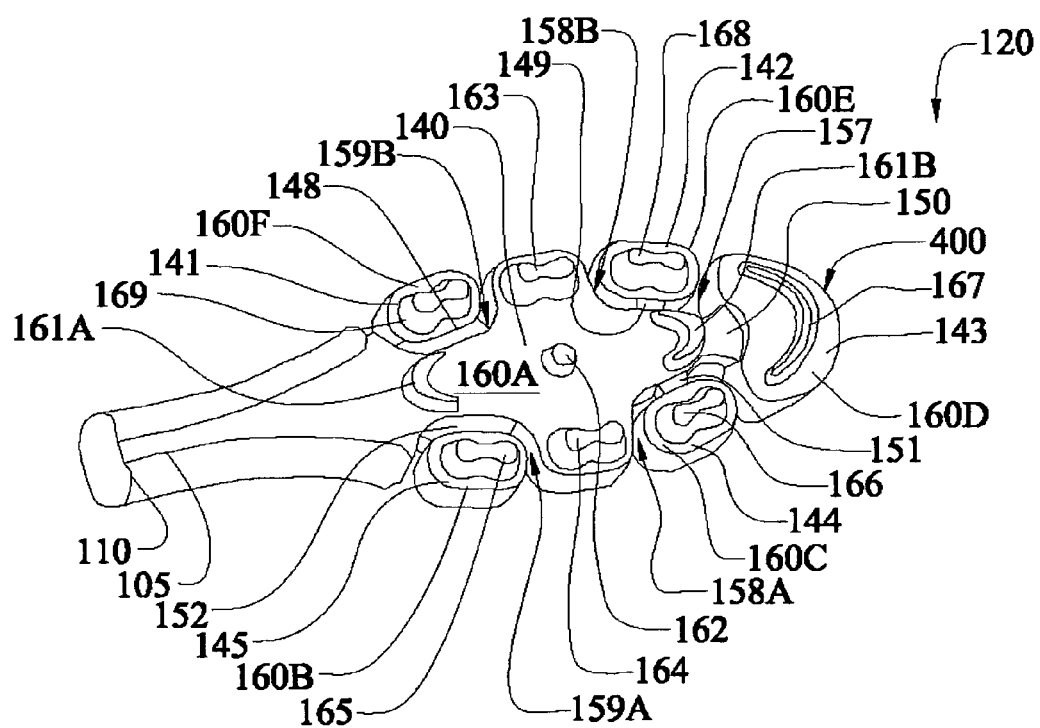
FIG. 7 is a rear perspective view of the rigid material skeleton of the head of the toothbrush of FIG. 1.
Figure 8:
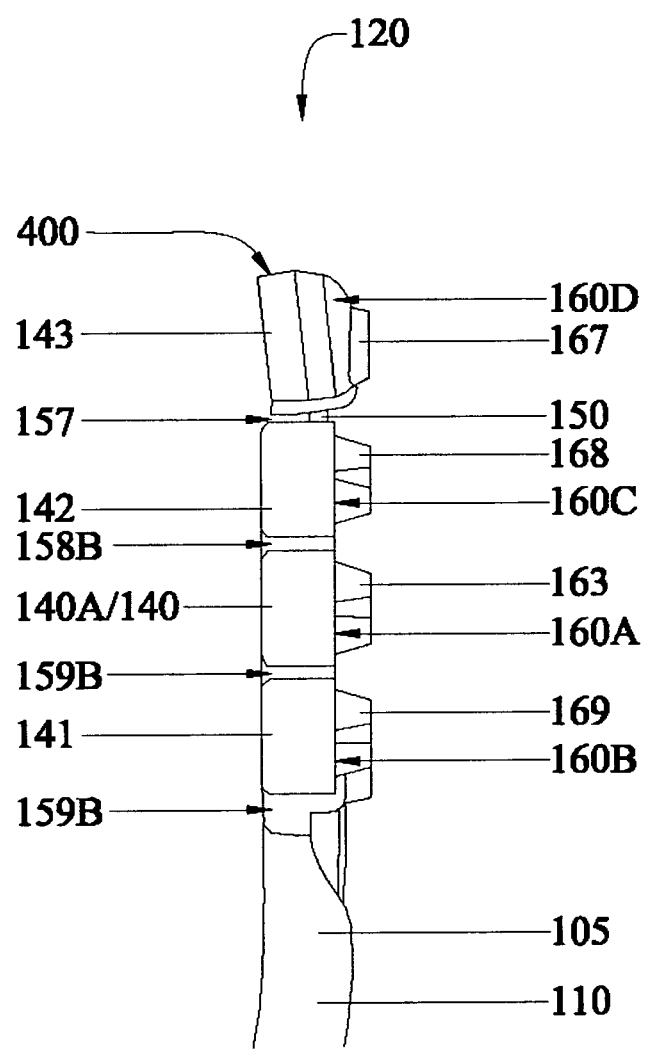
FIG. 8 is a side view of the rigid material skeleton of the head of the toothbrush of FIG. 1.
Figure 9:
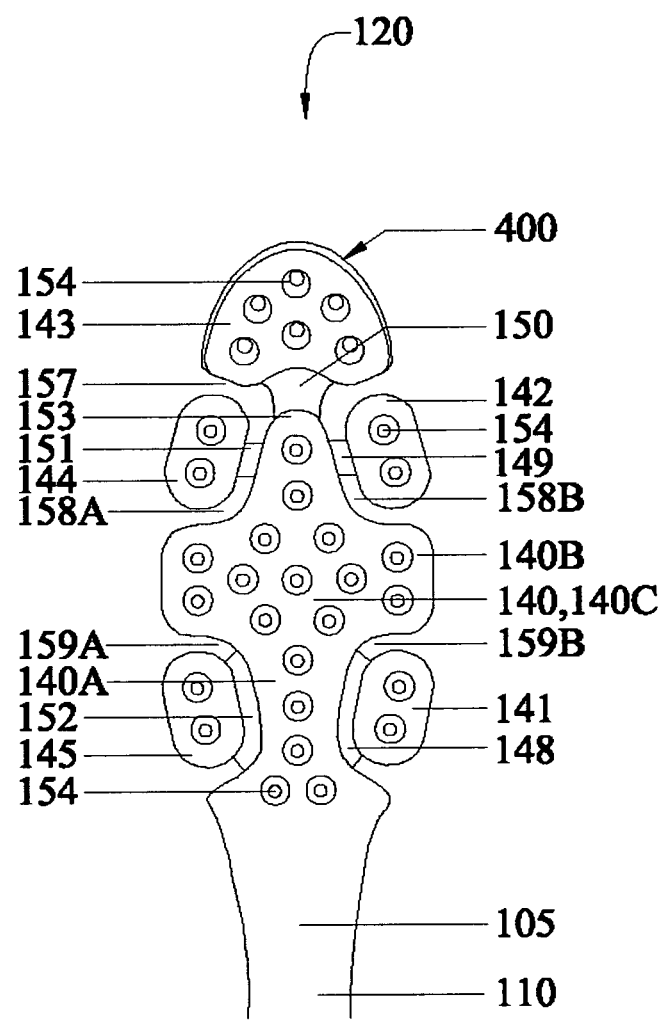
FIG. 9 is a front view of the rigid material skeleton of the head of the toothbrush of FIG. 1.
Figure 10:
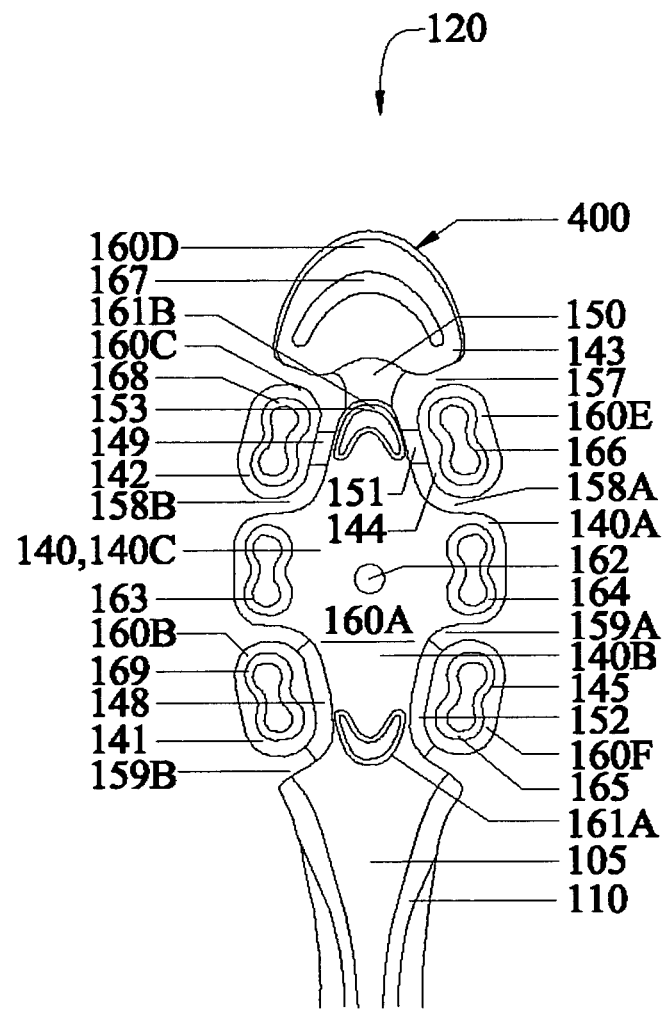
FIG. 10 is a rear view of the rigid material skeleton of the head of the toothbrush of FIG. 1.

Referring now to FIGS. 3-5 concurrently, the details of the head 120 will be described in accordance with one embodiment of the present invention. The head 120 of the toothbrush 100 extends along a longitudinal axis A-A. The head 120 generally comprises a plurality of spaced-apart segments 140-145. The plurality of segments 140-145 are constructed of a rigid material. In one embodiment, the plurality of segments 140-145 are formed of a hard plastic. Suitable hard plastics include, without limitation, polypropylene. In certain embodiments, the plurality of the segments 140-145 are formed of the same rigid material as the main structural component of the handle 110.

In the exemplified embodiment, the plurality of segments 140-145 include a central segment 140 and a plurality of peripheral segments 141-145. The central segment 140 is non-movably connected to the distal end 105 of the handle 110 in certain embodiments. For example, the central segment 140 may be integrally formed with the distal end 105 of the handle 110. In one specific embodiment, the main structural component of the handle 110 and a skeleton 400 (FIGS. 6-10) of the head 120 can be integrally formed in single injection molding step (which may use multi-ports for injecting the rigid material in liquid form).

The central segment 140 acts a hub to which the peripheral segments 141-145 are flexible connected. As discussed in greater detail below, each of the peripheral segments 141-145 are flexibly connected to the central segment 140 by an elastomeric material 146 that fills channels 157-159B (referring to FIG. 6, for example) formed between adjacent segments 140-145 and struts 148-152 that extend between the central segment 140 and the peripheral segments 141-145.

In the exemplified embodiment, the central segment 140 has a cruciform shape. Of course, the invention is not limited in all embodiments and may take on other shapes in certain other embodiments, including T-shaped, rectangular, oval, triangular, polygonal, or irregular. For purposes of discussion, the central segment 140 will be referred to as a cruciform segment 140 throughout the remainder of this written description because the exemplified embodiment is cruciform in shape. The cruciform segment 140 comprises a longitudinal portion 140A and a transverse portion 140B that intersect at a central juncture portion 140C. The longitudinal portion 140A extends along the longitudinal axis A-A in a coaxial alignment while the transverse portion 140B extends substantially perpendicular to the longitudinal axis A-A. In the exemplified embodiment, the transverse portion 140B extends the entire width of the head 120 (wherein the width of the head 120 is the distance between the right and left lateral edges 123, 124 measured substantially perpendicular to the longitudinal axis A-A) while the longitudinal portion 140A extends less than the entire length of the head 120 (wherein the length of the head 120 is the distance between a proximal end 147 of the head 120 (FIG. 6) to the distal edge 125 of the head 120 measured along the longitudinal axis A-A).

In the exemplified embodiment, the plurality of peripheral segments 141-145 comprises a distal segment 143, a first pair of segments 141, 145, and a second pair of segments 142, 144. The distal segment 143 is located at a distal end 153 of the cruciform segment 140. The first pair of segments 141, 145 are located on opposite sides of the longitudinal portion 140A of the cruciform segment 140. The second pair of segments 142, 144 are also located on opposite sides of the longitudinal portion 140A of the cruciform segment 140. However, the first pair of segments 141, 145 are located on an opposite side of a transverse portion 140B of the cruciform segment 140 than the second pair of segments 142, 144. Each of the segments 141-142, 144-145 of the first and second pairs are isolated from the cruciform segment 140 by the channels 158A-159B containing the elastomeric material 146. The distal segment 143 is also isolated from the cruciform segment 140 and the second pair of segments 142, 144 by a transverse channel 157 containing the elastomeric material 146. The various channels 157-159B will be described in greater below with respect to FIGS. 6-10.

Each of the plurality of segments 140-145 comprises a front surface 121A-121F. The front surfaces 121A-F of the segments 140-145 collectively form the front surface 121 of the head 120 in combination with the elastomeric material 146 of the channels. As will be described in greater below with respect to FIGS. 11-13, portions of the front surfaces 121A-C, 121E-F of the segments 140-142, 144-145 are covered (i.e., overlaid) by base portions of the elastomeric cleaning elements 132A-D. However, a substantial majority of the front surfaces 121A-F of the segments 140-145 remain exposed, thereby forming bristle regions from which the bristle tufts 131 extend from the segments 140-145. The rigid material of the segments 140-145 is exposed via the bristle regions and provide a sufficiently rigid structure to which the bristle tufts 131 can be secured.

Each of the segments 140-145 includes a plurality of bristle tufts 131 extending from the front surfaces 121A-F. In the exemplified embodiment, the bristle tufts 131 are secured to the segments 140-145 by anchoring the bristle tufts 131 in tuft holes 154 formed in the front surfaces 121A-F. The bristle tufts 131 can be anchored within the tuft holes 154 using staples, sonic welding, and other techniques known in the art. However, in alternate embodiments, the bristle tufts 131 can be secured to the segments 140-145 in any manner known in the art. For example, anchor free tufting (AFT) could be used to mount the bristle tufts 131. In AFT, a plate or membrane is secured to the segments 140-145, such as by ultrasonic welding. The bristle tufts 131 (or other tooth cleaning elements) extend through the plate or membrane. The free ends of the bristle tufts 131 on one side of the plate or membrane perform the cleaning function. The ends of the bristle tufts 131 on the other side of the plate or membrane are melted together by heat to be anchored in place.

The peripheral segments 141-142, 144-145 of the first and second pairs further comprise side surfaces 155A-D. Similarly, the transverse portion 140B of the cruciform segment 140 (which is also the central segment more generally) also comprises side surfaces 156A-B. Each of the side surfaces 155A-B of the peripheral segments 141-142 and the side surface 156A of the cruciform segment 140 form a portion of the right lateral edge 123 of the head 120. Similarly, the side surfaces 155C-D of the peripheral segments 144-145 and the side surface 156B of the cruciform segment 140 form a portion of the left lateral edge 124 of the head 120. The side surfaces 155A-D of the peripheral segments 141-142, 144-145 and the side surfaces 156A-B of the cruciform segment 140 are not covered by the elastomeric material 146 of the channels 157-159B, thereby remaining exposed.

Referring now to FIGS. 6-10 concurrently, the structure of the head 120 will be described in greater detail. In FIGS. 6-10, all of the elastomeric material 146 of the head 120 (including the elastomeric material 146 of the channels 157-159B, the elastomeric soft tissue cleaner 200, and the elastomeric cleaning elements 132A-E) has been removed, thereby exposing a skeleton 400 which is formed of the rigid material, such as a hard plastic, such as polypropylene. The skeleton 400 comprises the segments 140-145 and the struts 148-152. In one embodiment, the entirety of the skeleton 400 may be formed integrally as a unitary structure. However, in other embodiments, the components of the skeleton 400 may be formed separately and later assembled. Moreover, in certain alternative embodiments, one or all of the struts 148-152 may be omitted all together. In such an embodiment, the segments 140-145 would be flexibly connected together solely by the elastomeric material 146. Furthermore, while the exemplified embodiment of the head 120 of the present invention comprises six segments 140-145, in other embodiments, more or less segments may be used as desired.

As mentioned above, the segments 140-145 of the head 120 are spaced apart from one other. As a result, adjacent segments 140-145 of the head 120 are separated by one or more of the channels 157-159B. In the exemplified embodiment, the peripheral segment 141 is isolated from the cruciform segment 140 by the channel 159B while the peripheral segment 145 is isolated from the cruciform segment 140 by the channel 159A. The channels 159A-B may be curved channels. In the exemplified embodiment, the channels 159A-B are arcuate and take on a substantially U-shape. However, it is contemplated that the channels 159A-B can take on other appropriate shapes in other embodiments.

Similarly, the peripheral segment 142 is isolated from the cruciform segment 140 by a channel 158B while the peripheral segment 144 is isolated from the cruciform segment 140 by a channel 158A. The channels 158A-B may also be curved channels. In the exemplified embodiment, the channels 158A-B are arcuate and take on a substantially J-shape. However, it is contemplated that the channels 158A-B can take on other appropriate shapes in other embodiments. For example, the channels 158A-B may take on a substantially U-shaped and a portion of each of the channels 158A-B may coincide with a portion of the transverse channel 157.

The distal segment 143 is isolated from the cruciform segment 140 by a transverse channel 157. The transverse channel 157 also isolates the distal segment 143 from second pair of peripheral segments 142, 144. The transverse channel 157 is a curved channel. In the exemplified embodiment, the transverse channel 157 takes on a generally undulating shape. Moreover, the transverse channel 157 extends across the entire width of the head 120. In other words, the transverse channel 157 extends from the right lateral edge 123 to the left lateral edge 124 of the head 120. In some embodiments, a portion of the transverse channel 157 may coincide with a portion of the channel 158A. Similarly, in some embodiments, a portion of the transverse channel 157 may coincide with a portion of the channel 158B.

The struts 148-152 are disposed within the channels 157-159B and connect the peripheral segments 141-145 to the cruciform segment 140. Specifically, the strut 148 connects the segment 141 to the cruciform segment 140. The strut 149 connects the segment 142 to the cruciform segment 140. The strut 150 connects the distal segment 143 to the cruciform segment 140. The strut 151 connects the segment 144 to the cruciform segment 140. The strut 152 connects the segment 145 to the cruciform segment 140. While the foregoing description provides that one of the struts 148-152 connects one of the peripheral segments 141-145 to the cruciform segment 140, it is contemplated that more than one struts 148-152 or connection members may be used to connect the peripheral segments 141-145 to the cruciform segment 140.

Figure 12:
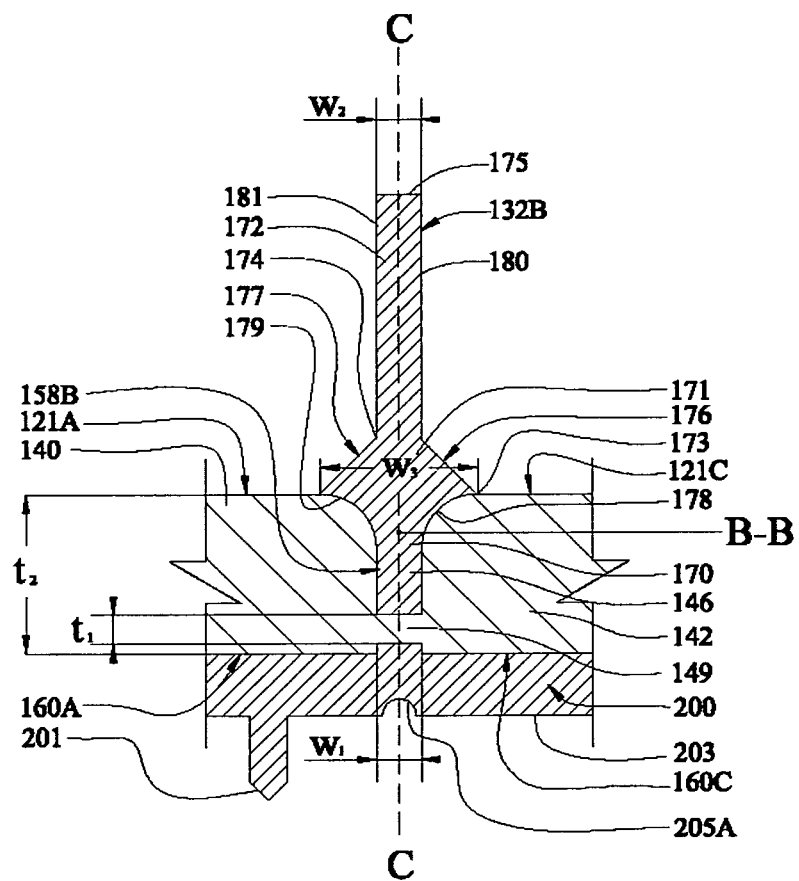
FIG. 12 is a cross-sectional view of the head of the toothbrush of FIG. 1 taken along line XII-XII of FIG. 11, wherein the segments are in a normal state.

The struts 148-152 are thin beam or thin shelf structures that extend between the peripheral segments 141-145 and the cruciform segment 140, thereby forming a flexible bridge therebetween. In one embodiment, the struts 148-152 are formed of a rigid material, such as a hard plastic, such as polypropylene. In a more specific embodiment, the struts 148-152 are formed of the same rigid material of which the segments 140-145 are formed, and possibly integrally formed therewith. While the struts 148-152 are constructed of what is considered a relatively rigid material in the art, flexibility of the struts 148-152 is still afforded by the thinned nature of the struts 148-152. For example, the struts 148-152 have a thickness $t_1$ (measured along an axis that is substantially perpendicular to the longitudinal axis A-A and passes through the front and rear surfaces) that is less than a thickness $t_2$ of the segments 140-145 (measured along an axis that is substantially perpendicular to the front surfaces 121A-F of the segments 140-145) (FIG. 12). In one embodiment, the ratio of $t_1:t_2$ is in a range of about 1:2 to about 1:5. Of course, the invention is not limited. When the channels 157-159B are filled with the ealstomeric material 146, the struts 148-152 are encapsulated within the elastomeric material 146.

Referring again to FIGS. 6-10, each of the segments 140-145 further comprises at least one protuberance extending from a rear surface 160A-F of the segments 140-145. In the exemplified embodiment, cruciform segment 140 comprises five protuberances, namely two arcuate ridges 161A-B, a central post 162, and two protuberances 163-164. Of course, more or less protuberances can be used as desired. The peripheral segment 141 comprises the protuberance 169. The peripheral segment 142 comprises the protuberance 168. The distal segment 143 comprises the protuberance 167. The peripheral segment 144 comprises the protuberance 166. The peripheral segment 145 comprises the protuberance 165. As will be discussed in greater detail below, one the purposes of the protuberances 161-169 is provide a contact surface for a mold used inject elastomeric material, in its liquid form, onto the skeleton 400 to fill the channels 157-159B, to form the elastomeric soft tissue cleaner 200, and to form the elastomeric cleaning elements 132A-E. Another purpose of one or all of the protuberances 161-169 is to provide an element that engages and/or scrapes soft oral tissue during use of the elastomeric soft tissue cleaner 200.

Referring now to FIGS. 4, 8, 10 and 12 concurrently, the oral care implement 100 further comprises an elastomeric soft tissue cleaner 200 located on the rear surface 122 of the head 120. The elastomeric soft tissue cleaner 200 is formed of an elastomeric material. The elastomeric material of the elastomeric soft tissue cleaner 200 may be any biocompatible resilient material suitable for uses in an oral hygiene apparatus. To provide optimum comfort as well as cleaning benefits, the elastomeric material preferably has a hardness property in the range of A8 to A25 Shore hardness. As an example, one preferred elastomeric material is styrene-ethylene/butylene-styrene block copolymer (SEBS) manufactured by GLS Corporation. Nevertheless, SEBS material from other manufacturers or other materials within and outside the noted hardness range could be used. In one embodiment, the elastomeric soft tissue cleaner 200 is integrally formed with the elastomeric material 146 of the channels 157-159B and the elastomeric cleaning elements 132A-E.

The elastomeric soft tissue cleaner 200 comprises a plurality of protuberances, in the form of nubs 201 and ridges 202, extending from a base surface 203 of the elastomeric soft tissue cleaner 200. As used herein a "nub" generally refers to a column-like protrusion (without limitation to the cross-sectional shape of the protrusion) which is upstanding from a base surface. In a general sense, the nub, in the preferred construction, has a height that is greater than the width at the base of the nub (as measured in the longest direction). Nevertheless, nubs could include projections wherein the widths and heights are roughly the same or wherein the heights are somewhat smaller than the base widths. Moreover, in some circumstances (e.g., where the nub tapers to a tip or includes a base portion that narrows to a smaller projection), the base width can be substantially larger than the height.

In one preferred arrangement of the elastomeric soft tissue cleaner 200, the nubs 201 are preferably conically shaped. As used herein, "conically shaped" or "conical" is meant to include true cones, frusto-conically shaped elements, and other shapes that taper to a narrow end and thereby resemble a cone irrespective of whether they are uniform, continuous in their taper, or have rounded cross-sections.

The protuberances 201, 202 of the elastomeric soft tissue cleaner 200 may help to significantly reduce a major source of bad breath in people and improve hygiene. The protuberances 201, 202 of the elastomeric soft tissue cleaner 200 enable removal of microflora and other debris from the tongue and other soft tissue surfaces within the mouth. The tongue, in particular, is prone to develop bacterial coatings that are known to harbor organisms and debris that can contribute to bad breath. This microflora can be found in the recesses between the papillae on most of the tongue's upper surface as well as along other soft tissue surfaces in the mouth. When engaged or otherwise pulled against a tongue surface, the nubs 201 of the elastomeric tissue cleaner 200 provide for gentle engagement with the soft tissue while reaching downward into the recesses of adjacent papillae of the tongue. The ridges 202 of the elastomeric tissue cleaner 200 then scrape the soft oral tissue surface, thereby removing the dislodged debris. The elastomeric construction of the elastomeric soft tissue cleaner 200 also enables the base surface 203 to follow the natural contours of the oral tissue surfaces, such as the tongue, cheeks, lips, and gums of a user. Moreover, the nubs 201 and ridges 202 are able to flex as needed to traverse and clean the soft tissue surfaces in the mouth along which it is moved.

In one embodiment, the elastomeric soft tissue cleaner 200 overlies the rear surfaces 160A-F of the segments 140-145. The protuberances 161A-169 of the segments 140-145 extend through the elastomeric soft tissue cleaner 200. Thus, a portion of each of the protuberances 161A-169 remains exposed on the rear surface 122 of the head 120. In the exemplified embodiment, the protuberances 161A-B, 162 of the cruciform segment 140 are substantially flush with the base surface 203 of the elastomeric soft tissue cleaner 200. However, the protuberances 163-169 of the segments 140-145 extend beyond and, thus, protrude from the base surface 203 of elastomeric soft tissue cleaner 200.

Whether the protuberances 161A-169 are flush or protrude from the base surface 163 of the elastomeric soft tissue cleaner 200, the exposed portions of the protuberances 161A-169 provide contact surfaces for the mold during injection molding of elastomeric soft tissue cleaner 200 to the skeleton 400. By providing a protuberance 161A-169 having an exposed portion on each of the segments 140-145, each of the segments 140-145 can be maintained in a stable orientation during the injection molding process that flows the elastomeric material 146 into the channels 157-159B, forms the elastomeric soft tissue cleaner 200, and/or forms the elastomeric cleaning elements 132A-E. Furthermore, the protuberances 163-169 of the segments 140-145 that protrude from the base surface 163 of the elastomeric soft tissue cleaner 200 work in coordinated manner with the protuberances 201, 202 of the elastomeric soft tissue cleaner 200 to engage and clean soft oral tissue.

Referring now to FIGS. 4, 12, 14 and 16 concurrently, it can be seen that the elastomeric soft tissue cleaner 200 further comprises a plurality of grooves 204, 205A, 205B formed in the base surface 203. As discussed in grater detail below, the plurality of grooves 204, 205A are aligned with the channels 157-159B, which contain the elastomeric material 146. More specifically, the plurality of grooves 204, 205A-B are aligned with the channels 157-159B so that an axis that is perpendicular to the longitudinal axis A-A (such as axis C-C of FIG. 12) intersects both the channels 157-159B and the grooves 204, 205A-B.

Figure 14:
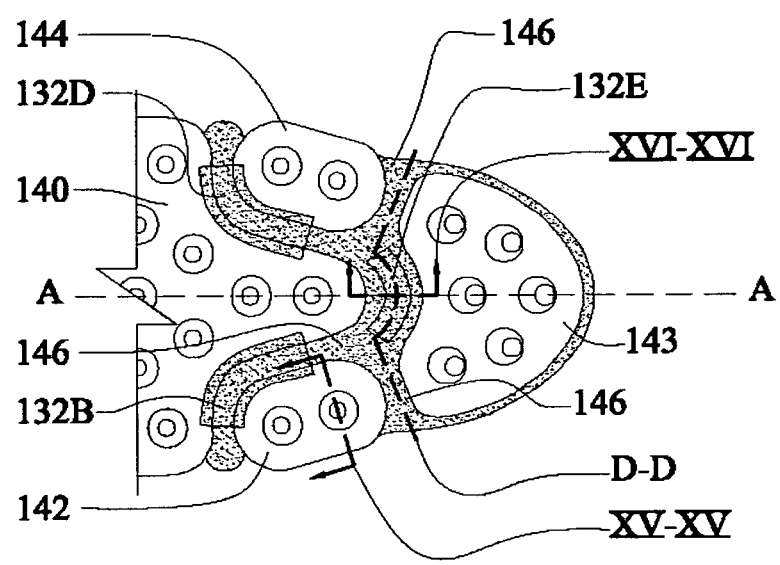
FIG. 14 is a close-up view of the distal portion of the head of FIG. 5.
Figure 15:
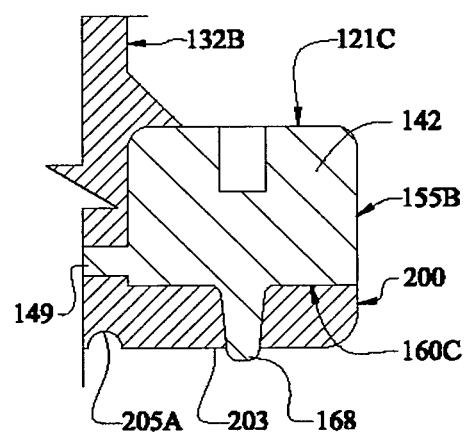
FIG. 15 is a cross-sectional view of the head of the toothbrush of FIG. 1 taken along line XV-XV of FIG. 14, wherein the segments are in a normal state.
Figure 16:
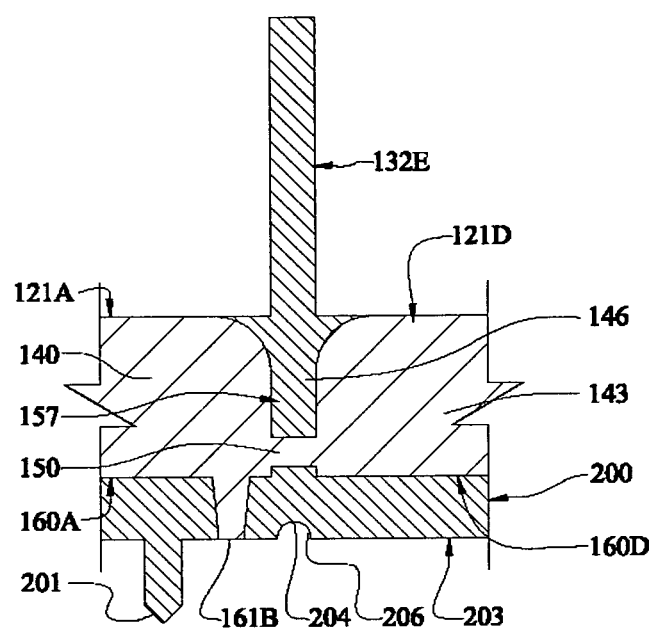
FIG. 16 is a cross-sectional view of the head of the toothbrush of FIG. 1 taken along line XVI-XVI of FIG. 14, wherein the segments are in a normal state.

In the exemplified embodiment, the elastomeric soft tissue cleaner 200 comprises a transverse groove 204 and two spaced-apart longitudinal grooves 205A, 205B. The transverse groove 204 extends transversely across the entire width of the head 120 from the right lateral edge 123 to the left lateral edge 124. The transverse groove 204 is aligned with the transverse channel 157 (best visible in FIG. 16). As a result, an axis that is perpendicular to the longitudinal axis A-A intersects both the transverse channel 157 and the transverse groove 204. As shown in FIGS. 12 and 14, the transverse channel 157 is nonlinear and extends generally along axis D-D. The transverse groove 204 also extends generally along axis D-D. The transverse groove 204 forms an upstanding transverse wall 206 that spans across the entire width of the head 120. This upstanding transverse wall 206 further assists with soft tissue cleaning when the elastomeric soft tissue cleaner 200 is dragged across a soft oral tissue by creating an additional scraping ridge. Moreover, the transverse nature of the groove 204 further assists during soft tissue cleaning by channeling fluid and dislodged debris to the lateral edges 123, 124 where it escapes from the elastomeric soft tissue cleaner 200 and does not become pressed back into the soft tissue. In addition to assisting with soft tissue cleaning, the transverse groove 204, by nature of being aligned with the transverse channel 157, also assist with tooth cleaning by providing an added amount of flexibility to the distal segment 143 relative to the cruciform segment 140.

The longitudinal grooves 205A, B extend longitudinally from the transverse groove 204 toward the proximal end 147 of the head 120, terminating at the right and left lateral edges 123, 124 of the head 120 adjacent the proximal end 147. The longitudinal groove 205A is aligned with portions of both the channel 158B and the channel 159B (FIG. 12). The longitudinal groove 205B is aligned with portions of both the channel 158A and the channel 159A. Similar to the transverse groove 204, the longitudinal grooves 205A, B assist with soft tissue cleaning by channeling fluid and dislodged debris to the lateral edges 123, 124 where it escapes from the elastomeric soft tissue cleaner 200 and does not become pressed back into the soft tissue. The longitudinal channels 205A, B terminate at locations on the right and left lateral edges 123, 124 closer to the proximal end 147 of the head 120 than does the transverse groove 204 such that the fluids and debris are dispensed at different locations so as to prevent clogging. Moreover, by nature of being aligned with the channels 158B, 159B, the longitudinal groove 205A assists with tooth cleaning by providing an added amount of flexibility to the peripheral segments 141, 142 relative to the cruciform segment 140. Similarly, by nature of being aligned with the channels 158A, 159A, the longitudinal groove 205B assists with tooth cleaning by providing an added amount of flexibility to the peripheral segments 144, 145 relative to the cruciform segment 140.

Figure 11:
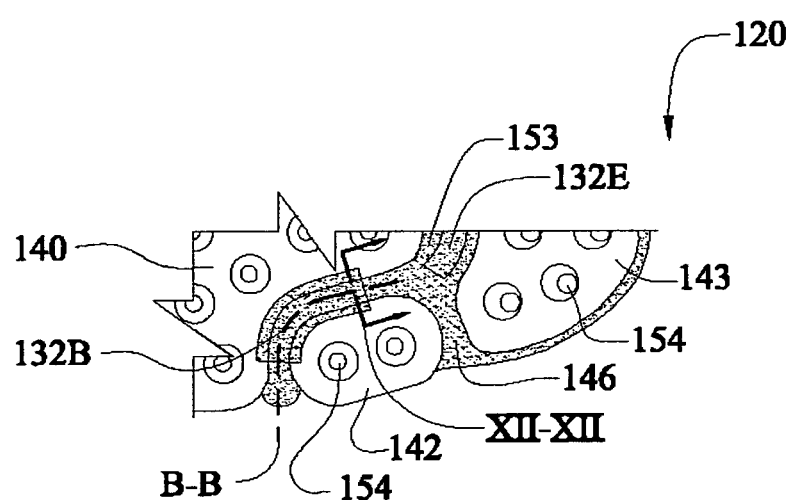
FIG. 11 is a close-up view of a quadrant of the head of FIG. 5.

Referring now to FIGS. 3, 11 and 12 concurrently, one embodiment of an elastomeric cleaning element and its structural cooperation with the head 120 will be described. For purposes of discussion, the following description will refer to the elastomeric cleaning element 132B as an elastomeric wall 132B because the exemplified embodiment depicts a wall. While the embodiment of the elastomeric cleaning element will be described in relation to the elastomeric wall 132B and its interaction with the channel 158B and the elastomeric material 146 contained therein, it is to be understood that the discussion below is applicable to the other elastomeric walls 132A, 132C, 132D and their interaction with the channels 159B, 159A, 158A and the elastomeric material 146 contained therein. Moreover, while the invention will be discussed in terms of an elastomeric wall, it is to be understood that the principles discussed below could be applied to elastomeric fingers and other elastomeric structures in other embodiments.

Figure 13:
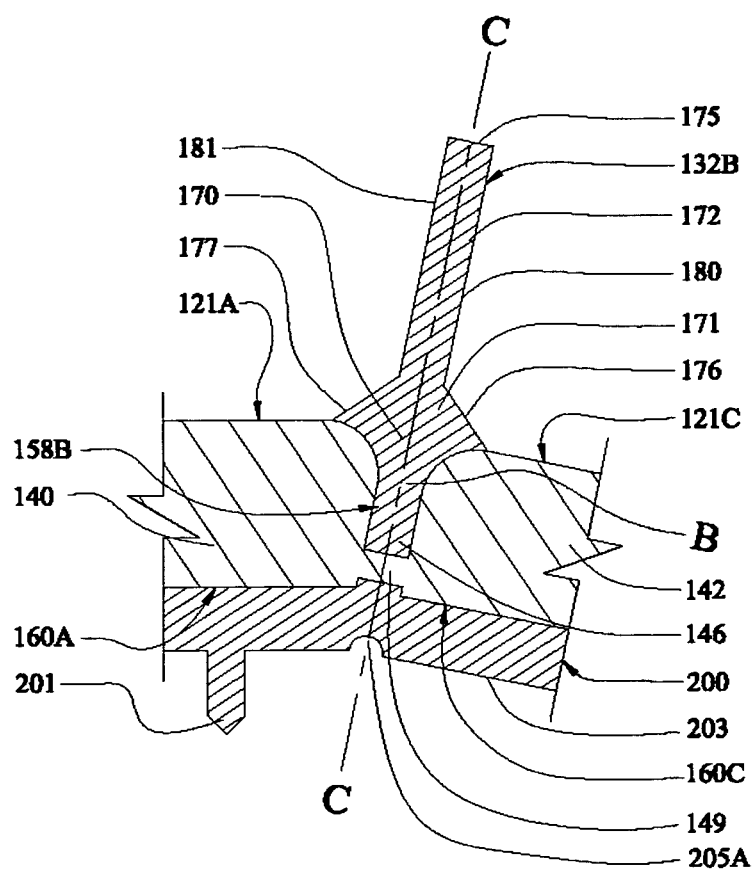
FIG. 13 is a cross-sectional view of the head of the toothbrush of FIG. 1 taken along line XII-XII of FIG. 11, wherein the segments are in a flexed state.

The elastomeric wall 132B is an arcuate wall that extends along the curved channel 158B. More specifically, the channel 158B extends along curved axis B-B. In the exemplified embodiment, the elastomeric wall 132B also extends along the curved axis B-B and extends upward from the front surface 121 of the head 120 along an axis C-C. In FIG. 12, the segments 140, 142 of the head 120 are in a normal state (i.e., a state in which no forces are applied to the head 120). In the normal state, the segments 140, 142 are not flexed relative to one another and the surfaces 121A, 121C of the segments are substantially coplanar. In FIG. 13, the segments 140, 142 of the head 120 are in a flexed state (i.e., a state in which forces imparted during normal brushing are applied to the head 120). In the flexed state, the segments 140, 142 are flexed relative to one another so that the surfaces 121A, 121C are moved into a non-coplanar arrangement. Upon cessation of brushing forces, the elastomeric material 146 of the channel 158B and the strut 149 bias the segments 140, 142 back into the normal state. The invention, however, is not limited to instances where the front surfaces 121A, 121C are in a coplanar arrangement in the normal state and flexed into a non-coplanar arrangement in the flexed state. In certain alternative embodiments, the front surfaces 121A, 121C could be in a non-coplanar arrangement in the normal state and flexed into a arrangement in the flexed state. In still another alternative embodiment, the front surfaces 121A, 121C could be in a first non-coplanar arrangement (i.e., at a first angle relative to one another) in the normal state and flexed into a second non-coplanar arrangement (i.e., at a second different angle relative to one another) in the flexed state. It is contemplated that the arrangement of the front faces 121A, 121C in the normal state and the flexed state can be altered, if desired.

Referring to FIG. 12, the elastomeric wall 132B generally comprises a root portion 170, a base portion 171 and an upper portion 172. The root portion 170 is disposed within the channel 158B and connected to the elastomeric material 146 within the channel 158B. The root portion 170 extends upward from the elastomeric material 146 along an axis C-C and connects to a lower end 173 of the base portion 171. The base portion 171 extends upward along the axis C-C from the lower end 173 to an upper end 174. The upper portion 172 of the elastomeric wall 132B extends upward along the axis C-C from the upper end 174 of the base portion 171 to a terminal end 175. In the exemplified embodiment, the terminal end 175 is flat. However, in other embodiments, the terminal end 175 can be rounded or tapered, or be in the form of other suitable shapes.

The lower end 173 of the base portion 171 of the elastomeric wall 132B has a width $W_3$, measured perpendicular to the axis B-B. The upper end 174 of the base portion 171 of the elastomeric wall 132B has a width $W_2$, measured perpendicular to the axis B-B. The width $W_2$ is less than the width $W_3$. The width $W_3$ of the lower end 173 of the base portion 171 of the elastomeric wall 132B is greater than the width $W_1$ of the channel 158B, measured perpendicular to the axis B-B. As a result of the width $W_3$ being greater than the width $W_1$, the lower end 173 of the base portion 171 overlies portions 178, 179 of the front surfaces 121C, 121A of the segments 142, 140 respectively. The remainder of the front surfaces 121C, 121A of the segments 142, 140 remain exposed.

In the exemplified embodiment, the base portion 171 comprises two oblique surfaces 176, 177 and, thus, the base portion 171 gradually tapers in width from the lower end 173 to the upper end 174. In alternate embodiments, the base portion 171 may include stepped surfaces rather than the two oblique surfaces 176, 177. In such an embodiment, the base portion 171 would taper in a stepped manner rather than gradually.

The upper portion 172 of the elastomeric wall 132B comprises a first major surface 180 and a second major surface 181 that is opposite to the first major surface 180. In the exemplified embodiment, the first and second major surfaces 180, 181 are substantially parallel to one another, thereby resulting in the upper portion 172 having a constant width $W_2$ along its height. In certain embodiments, the width $W_2$ will be equal to or less than the width $W_1$ of the channel 158B. In one specific embodiment, the width $W_2$ may be substantially equal to the width $W_1$ of the channel 158B.

By designing the elastomeric wall 132B so that the base portion 171 is wider than the upper portion 172, the upper portion 172 remains flexible so that it can wipe the surfaces of teeth. However, the base portion 171 will provide structural integrity and helps prevent excessive wear/bending of the elastomeric wall 132B. Moreover, by connecting the lower end 173 of the base portion 171 to the portions 178, 179 of the front surfaces 121C, 121A of the segments 142, 140, the elastomeric wall 132B will assist in preventing over-flexing of the segments 142, 140 relative to one another while being imparted with extra motion induced by said limited flexing between the segments 142, 140.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

While the foregoing description and drawings represent the exemplary embodiments of the present invention, it will be understood that various additions, modifications and substitutions may be made therein without departing from the spirit and scope of the present invention as defined in the accompanying claims. In particular, it will be clear to those skilled in the art that the present invention may be embodied in other specific forms, structures, arrangements, proportions, sizes, and with other elements, materials, and components, without departing from the spirit or essential characteristics thereof. One skilled in the art will appreciate that the invention may be used with many modifications of structure, arrangement, proportions, sizes, materials, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being defined by the appended claims, and not limited to the foregoing description or embodiments.

What is claimed is:

1. An oral care implement comprising:
   a handle;
   a head connected to the handle;
   a plurality of tooth cleaning elements extending from a front surface of the head;
   the head formed by a plurality of spaced-apart segments formed of a rigid material, the plurality of segments including a central segment and at least one peripheral segment arranged about the central segment, the at least one peripheral segment isolated from the central segment by a channel containing an elastomeric material, the elastomeric material flexibly connecting the at least one peripheral segment to the central segment;
   an elastomeric soft tissue cleaner located on a rear surface of the head opposite the front surface of the head;
   the at least one peripheral segment comprising at least one protuberance formed of the rigid material that extends through and protrudes beyond a base surface of the elastomeric soft tissue cleaner so that a portion of the rigid material of the at least one protuberance is exposed; and
   the central segment comprising a first protuberance that extends through and protrudes beyond the base surface of the elastomeric soft tissue cleaner and a second protuberance that extends through and is flush with the base surface of the elastomeric soft tissue cleaner.

2. The oral care implement according to claim 1 wherein the central segment is integrally formed with and extends from a distal end of the handle.

3. The oral care implement according to claim 1 wherein the plurality of tooth cleaning elements comprises a plurality of elastomeric walls integrally formed with the elastomeric material of the channel.

4. The oral care implement according to claim 1 wherein the plurality of tooth cleaning elements comprises a plurality of bristle tufts extending from the at least one peripheral segment and the central segment.

5. The oral care implement according to claim 1 wherein the elastomeric soft tissue cleaner is integrally formed with the elastomeric material of the channel.

6. The oral care implement according to claim 1 wherein the at least one peripheral segment is further connected to the central segment by a strut disposed within the channel that is formed of the rigid material.

7. The oral care implement according to claim 6 wherein the strut is integrally formed with the central segment and the at least one peripheral segment.

8. The oral care implement according to claim 6 wherein the strut has a first thickness and the central segment and the at least one peripheral segment have a second thickness, wherein the first thickness is less than the second thickness.

9. The oral care implement according to claim 6 wherein the strut is encapsulated in the elastomeric material of the channel.

10. The oral care implement of claim 1 wherein the elastomeric soft tissue cleaner comprises protuberances extending from the base surface of the elastomeric soft tissue cleaner.

11. The oral care implement according to claim 10 wherein the elastomeric soft tissue cleaner further comprising at least one groove formed in the base surface, and wherein the at least one groove of the elastomeric soft tissue cleaner is aligned with the channel.

12. An oral care implement comprising:
    a handle;
    a head connected to the handle;
    a plurality of tooth cleaning elements extending from a front surface of the head;
    the head formed by a plurality of spaced-apart segments formed of a rigid material, each of the segments isolated from one another by a channel containing an elastomeric material, the elastomeric material flexibly connecting the segments together;
    an elastomeric soft tissue cleaner located on a rear surface of the head opposite the front surface of the head;
    each of the segments comprising at least one protuberance formed of the rigid material that extends through and protrudes beyond a base surface of the elastomeric soft tissue cleaner so that a portion of the rigid material of the at least one protuberance is exposed; and
    one of the segments comprising another protuberance that extends through and is flush with the base surface of the elastomeric soft tissue cleaner.

13. The oral care implement according to claim 12 wherein the plurality of segments includes a central segment and a plurality of peripheral segments arranged about the central segment, and wherein the central segment is non-movably connected to a distal end of the handle.

14. The oral care implement according to claim 12 wherein the plurality of tooth cleaning elements comprises a plurality of elastomeric walls integrally formed with the elastomeric material of the channels.

15. The oral care implement according to claim 14 wherein the elastomeric walls, the elastomeric material of the channels, and the elastomeric soft tissue cleaner is an integral mass of elastomeric material.

16. The oral care implement according to claim 12 wherein the plurality of tooth cleaning elements comprises a plurality of bristle tufts extending from each of the segments.

17. The oral care implement according to claim 12 wherein the elastomeric soft tissue cleaner is integrally formed with the elastomeric material of the channels.

18. The oral care implement according to claim 12 wherein each of the segments is further connected to one another by a strut disposed within the channel that is formed of the rigid material, and wherein the struts are integrally formed with the segments.

19. An oral care implement comprising:
    a handle;
    a head connected to the handle;
    a plurality of tooth cleaning elements extending from a front surface of the head;
    the head formed by a skeleton formed of a rigid material, the skeleton comprising a plurality of spaced-apart segments and struts extending between the segments;

an elastomeric material flexibly connecting the segments together;

an elastomeric soft tissue cleaner located on a rear surface of the head opposite the front surface of the head;

each of the segments comprising at least one protuberance formed of the rigid material that extends through and protrudes beyond a base surface of the elastomeric soft tissue cleaner so that a portion of the rigid material of the at least one protuberance is exposed; and one of the segments comprising another protuberance that extends through and is flush with the base surface of the elastomeric soft tissue cleaner.

20. The oral care implement according to claim 19 wherein the elastomeric soft tissue cleaner is integrally formed with the elastomeric material that flexibly connects the segments together.

21. The oral care implement according to claim 20 wherein the elastomeric soft tissue cleaner and the elastomeric material that flexibly connects the segments together is applied to the skeleton during a single injection molding step.

* * * * *